United States Patent [19]
Cohen

[11] 3,933,870
[45] Jan. 20, 1976

[54] SYNTHESIS OF A-RING AROMATIC STEROIDS
[75] Inventor: Noal Cohen, Montclair, N.J.
[73] Assignee: Hoffmann-La Roche Inc., Nutley, N.J.
[22] Filed: Sept. 30, 1974
[21] Appl. No.: 510,262

Related U.S. Application Data
[60] Division of Ser. No. 375,558, July 2, 1973, which is a continuation-in-part of Ser. No. 295,032, Oct. 4, 1972, abandoned.

[52] U.S. Cl............................ 260/397.5; 260/397.4
[51] Int. Cl.² ......................... C07J 9/00; C07J 1/00
[58] Field of Search ............................... 260/397.5; /Machine Searched Steroids

[56] References Cited
UNITED STATES PATENTS

| | | | |
|---|---|---|---|
| 3,475,468 | 10/1969 | Stein et al. | 260/397.45 |
| 3,707,490 | 12/1972 | Edwards et al. | 260/397.45 |
| 3,856,864 | 12/1974 | Cohen | 260/397.5 |

*Primary Examiner*—Elbert L. Roberts
*Attorney, Agent, or Firm*—Samuel L. Welt; Jon S. Saxe; Raymond R. Wittekind

[57] ABSTRACT

Total synthesis of steroids of the estrone and equilenin series involving conjugate 1,4-addition of a meta-substituted benzyl organometallic reagent to a C/D bicyclic methylene ketone. An aromatization of the B-ring of Δ 9(11) estrone derivatives.

4 Claims, No Drawings

SYNTHESIS OF A-RING AROMATIC STEROIDS

RELATED APPLICATIONS

This application is a division of copending U.S. patent application Ser. No. 375,558, filed July 2, 1973, which in turn is a continuation-in-part of U.S. patent application Ser. No. 295,032, filed Oct. 4, 1972, now abandoned.

BRIEF DESCRIPTION OF THE INVENTION

The present invention relates to a process for the preparation of steroids starting with a C/D bicyclic intermediate. In particular, the types of steroids which may be synthesized by means of the present process are those having an aromatic A-ring such as estrone, estrone methyl ether, and so forth; and those steroids having both the A and B-ring aromatic such as equilenin and equilenin methyl ether. Aromatic steroids such as those aforementioned are naturally occurring hormones which possess a wide range of biological activity and are also useful for the preparation of other compounds of the steroid type, for example, 19-norsteroids.

As used throughout the specification and the appended claims, the term "lower alkyl" denotes a saturated group consisting solely of carbon and hydrogen having a straight chain of from 1 to 8 carbon atoms. Examples of such groups are methyl, ethyl, butyl, hexyl, octyl, and the like. The term "tertiary lower alkyl" denotes a saturated group consisting solely of carbon and hydrogen having its valence from a carbon bound to three other carbon atoms. Examples of such groups include tertiary butyl, tertiary amyl, and so forth. The term "halogen" refers to chlorine, bromine and iodine and the term "halide" refers to the negative ions thereof. The term "lower alkylene" refers to a divalent saturated hydrocarbon group having its two valences to two different groups. Examples of such groups are methylene, ethylene, 1,2-propylene, 1,3-propylene, 1,4-butylene, 1,5-pentylene, and so forth.

In the formulae presented herein, the relative stereochemistry of the various substituents on the cyclic nucleus is indicated by one of three notations: a solid line (———), indicating the substituent is in the β-orientation, i.e., above the plane of the molecule: a dotted line (-----), indicating the substituent is in the α-orientation, i.e., below the plane of the molecule; or a wavy line (∼∼∼), indicating the substituent may be either in the α- or β-configuration or may be a mixture of both.

For convenience, the stereochemistry of the substituent R at the C-13 position has been arbitrarily indicated as the β-orientation; thus all the compounds are depicted a having the natural absolute configuration. It should be understood that the invention described herein is equally applicable to compounds having either the natural or the unnatural configuration, for example, to racemic mixtures.

If it is desired to prepare optically active steroids, one may either begin with a known optically active comound of Formula I

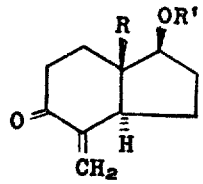

I wherein
R is lower alkyl
R' is tertiary lower alkyl,
or a group of the formula

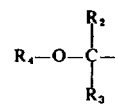

wherein
$R_2$ is hydrogen or lower alkyl,
$R_3$ and $R_4$ each taken independently are lower alkyl, and
$R_3$ and $R_4$ taken together are lower alkylene of from 3 to 6 carbon atoms, or alternatively, one may start with a racemic compound of Formula I and may carry out an optical resolution at one of the intermediate stages, or at the stage of the final product by methods known per se.

Among the groups that may be specifically mentioned for R' are tert-butyl, tetrahydrofuran-2-yl, tetrahydropyran-2-yl, methoxymethyl, 2-(2-methoxy)-isopropyl, and so forth.

In the process of the present invention, it is preferred that R, i.e., the substituent in the 13-position, be methyl or ethyl, most preferably, methyl; and that the substituent R' be tertiary butyl.

The first step in the present process involves the conjugate 1,4-addition of a meta substituted benzyl moiety derived from an organometallic agent of the formula

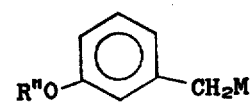

wherein R'' is lower alkyl, tertiary lower alkyl, benzyl, diphenylmethyl or trityl, and M is magnesium halide, lithium or copper, to a methylene ketone of the Formula I. In this step, all of the carbon atoms necessary to form the steroid nucleus are combined into the steroid precursor of Formula II

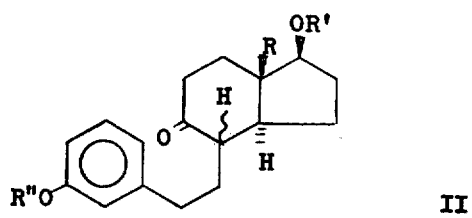

II wherein R, R' and R'' are as above.

It is preferred that the R'' substituent on the organometallic agent be methyl or benzyl.

Methylene ketones of Formula I are well-known compounds in the literature (see, for example, British Pat. No. 1,244,918) and have been used as versatile intermediates for other types of steroid synthesis. The metallic groups represented by M are magnesium halide, lithium and copper and the reagents prepared therefrom are referred to, respectively, as Grignard reagents, organolithium reagents and organocopper reagents. Preparation of Grignard reagents and organolithium reagents from the corresponding substituted benzyl halides is by methods known per se (reaction with magnesium or lithium metal), and these reagents prepared in situ may be used directly for the addition reaction. The use of Grignard reagents is preferred.

The addition reaction of the organometallic reagent, where M is magnesium halide or lithium, to the methylene ketone is carried out in the presence of cuprous ion. The cuprous ion is conveniently derived from a cuprous halide, most preferably having the same halogen as that from which the organometallic reagent was prepared. The amount of cuprous halide utilized in the present reaction can vary from less that 1 mole % up to about 500 mole % with respect to methylene ketone I. The use of between about 50 and 300 mole % cuprous halide is preferred.

It is believed that the Grignard or organolithium reagent reacts with the cuprous ion to form a organocopper reagent (M is copper) in situ and that it is this species which adds to the methylene ketone.

Organometallic reagents when M is copper (organocopper reagents) may also be pre-formed by reaction of a Grignard or organolithium reagent with a cuprous halide. The pre-formed reagent may then be used to react with the methylene ketone of Formula I.

Suitable solvents for the present addition reaction are inert organic solvents and include organic ethers, e.g., diethyl ether or tetrahydrofuran; hydrocarbons, e.g., pentane, hexane, toluene, and so forth; or mixtures of the above. If a Grignard reagent is utilized, it is most preferable to employ a solvent consisting mainly of an ether, whereas, if an organolithium reagent is utilized, it is most preferable to use a solvent consisting mainly of hydrocarbons, since these are normally solvents in which the reagents are prepared.

The temperature of the addition reaction is not critical, but it is preferred to employ a temperature between about −30° and +30°C. Normally, to achieve the best results, it is preferable to use an excess of the organometallic reagent over over the methylene ketone. A molar excess of from about 5 to 10 fold is especially preferred.

After the completion of the addition reaction, the reaction mixture is hydrolyzed in an aqueous medium. It is preferred that the aqueous medium contain an acid, most preferably a mineral acid such as sulfuric or hydrochloric acid. In this manner, metallic slats of the product, as well as any excess organometallic reagent, are decomposed and the reaction product can be easily isolated, for example, by extraction.

The compound of Formula II is normally produced in two epimeric forms: a 4 α-H (axial side chain) and a more stable 4 β-H (equatorial side chain) form. The former epimer can be isomerized, if desired, to the latter (more stable) one by base treatment, e.g., by treatment with an alkali metal hydroxide at elevated temperature, thus avoiding a physical separation of these epimers by, e.g., chromatography.

In the next step, the addition product (II), where R' is tertiary lower alkyl can be cyclized to a tetracyclic steroid (IIIa)

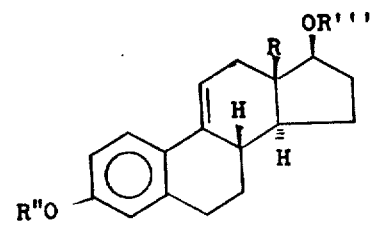

IIIa wherein R and R'' are as above, and R''' is tertiary lower alkyl,
without loss of the protecting group in the 17-position. Suitable conditions for this cyclization involve the treatment of compound II with a mineral acid or organic sulfonic acid at low temperature. Either pure 4 β-H epimer of Formula II, or a mixture of epimers can be used for this reaction.

Suitable acids for the practice of this cyclization include mineral acids such as hydrochloric acid, hydrobromic acid, sulfuric acid, and the like; and sulfonic acids such as methanesulfonic acid or p-toluenesulfonic acid, and the like. The concentration of the acid in the total reaction medium should not exceed 4 N and can be as low as 0.5 N. Suitable solvents for this cyclization reaction include alcohols such as methanol and ethanol, and mixtures of the above in water.

The temperature of the cyclization reaction is somewhat critical and care must be taken that the temperature be kept between about 0° and about 30°C, so that the protecting group in the 17-position is not hydrolyzed.

Where R' is other than tertiary lower alkyl, the compound of formula II can be cyclized to that of Formula +

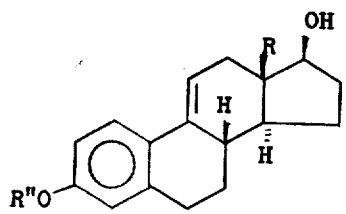

IIIb wherein R and R'' are as above.
In this case, the R' group is cleaved to afford a 17β hydroxy group. The reaction conditions can be the same as for the conversion II → IIIa, or the temperature and acid concentration can be higher, for example, temperatures up to about 100° may be employed.

Compounds of Formulas IIIa or IIIb can then be converted to known steroids such as estrone methyl ether by a further sequence of reactions.

Starting with a compound of Formula IIIa the 9(11) double bond is reduced to afford the compound of Formula IV

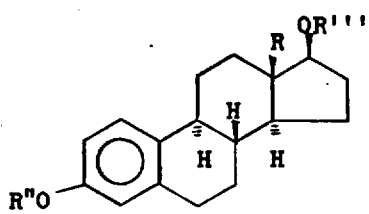

IV wherein R, R'' and R''' are as above.

Methods for reduction of this double bond are known per se and include catalytic hydrogenation, for example, hydrogenation over a palladium on carbon catalyst in an inert organic solvent such as ethyl acetate. Alternatively, the double bond can be chemically reduced using well-known conditions such as lithium in ammonia in the presence of an added amine such as aniline.

The protective tertiary lower alkyl group R''' can be removed in the next step by treatment with a strong acid to afford a compound of formula V

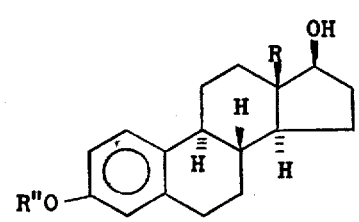

V wherein R and R'' are as above.

Suitable methods for removing this protecting group include treatment of the compound with a mineral acid such as hydrochloric acid or sulfuric acid or with an organic sulfonic acid such as p-toluene sulfonic acid at elevated temperature, for example, between about 50° and 100° C in a suitable solvent, for example, a hydrocarbon such as toluene. Alternatively, the protecting group can be removed by treatment with trifluoroacetic acid at a low temperature, for example, about 0° to about 30°C, followed by alkali treatment to remove any trifluoroacetate ester formed.

Alternatively, a compound of Formula V can be prepared directly from a compound of Formula IIIb by catalytic hydrogenation or chemical reduction, as described above for the conversion IIIa → IV.

The 3-ether of estradiol (V) can be converted to the corresponding 17-ketone VI

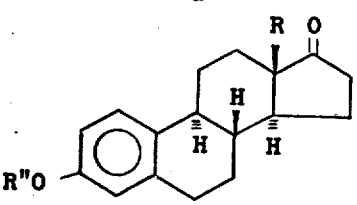

VI wherein R and R'' are as above,
by standard oxidation techniques such as oxidation with chromium VI compounds, for example, Jones reagent, according to methods known per se.

It has been discovered that where R' is a tertiary lower alkyl protecting group, its removal from compound IIIa (which still contains the 9(11) double bond) leads to a novel and unexpected aromatization of the B-ring leading to equilenin derivaties of Formula VII

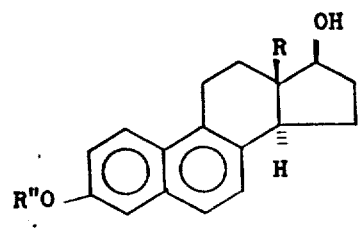

VII wherein R and R'' are as above.

This reaction may be carried out in one embodiment by treatment of the compound of Formula IIIa with a mineral acid such as hydrochloric acid or sulfuric acid, or with an organic sulfonic acid such as p-toluenesulfonic acid. Best results are achieved at elevated temperatures, for example, between about 50° and 100°C. Suitable solvents for this reaction include, for example, alcohols such as methanol and ethanol, and mixtures of the above with water.

An alternative method for cleavage of the tertiary lower alkyl group with concomitant aromatization of the B-ring involves reaction with trifluoroacetic acid. In this reaction, the compound of Formula III is treated with an excess of trifluoroacetic acid, preferably at a temperature between about −10° and +20°C, most preferably about 0°C. It is most advantageous to perform this reaction in neat trifluoroacetic acid, i.e., without the addition of other solvents, since trifluoroacetic acid is quite volatile and excesses can be easily removed and recovered, for example, by distillation. The initial product obtained from this reaction is the 17-trifluoroacetate of the compound of Formula VII. Due to the lability of the trifluoroacetate ester, it is preferred to immediately convert this product during the workup of the reaction to the corresponding 17-hydroxy compound by treatment with water in the presence of a base.

Suitable basis include alkali metal bicarbonates, e.g., sodium or potassium bicarbonate; alkali metal carbonates, e.g., sodium or potassium carbonate; or alkali metal hydroxides such as sodium or potassium hydroxide. Alkali metal hydroxides are preferred. This hydrolysis is conveniently effected by stirring the crude reaction product, after removal of the excess trifluoroacetic acid, with a mixture of aqueous base and a suitable water miscible or semi-miscible solvent. Preferable solvents for this purpose include alcohols such as methanol and ethanol; ethers such as tetrahydrofuran and dioxane; and ketones such as acetone. The crude product of Formula VII can be converted to equilenin 3-lower alkyl ethers VIII (for example, equilenin methyl ether, where R'' is methyl)

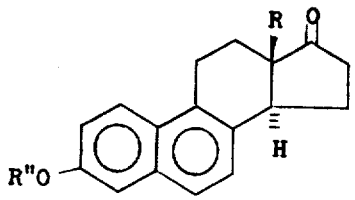

VIII wherein R and R'' are as above,
by standard oxidation techniques such as oxidation with a chromium VI reagent, for example, Jones reagent, according to methods known per se.

The present processes may be more fully understood by reference to the following illustrative examples:

EXAMPLE 1 (+)-1β-tert.

Butoxy-3aα,4β,7,7a-tetrahydro-4α-[2-(3-methoxyphenyl)ethyl]-7aβ-methyl-5(6H)-indanone A solution of 15.7 g (0.1 mole) of m-methoxybenzyl chloride dissolved in 100 ml of anhydrous tetrahydrofuran was added dropwise over a period of 1.5 hr. to a rapidly stirred suspension of 9.7 g (0.4 mole) of magnesium turnings in 100 ml of anhydrous tetrahydrofuran, iwth ice bath cooling, under an argon atmosphere. The ice bath was removed and the mixture was stirred while warming to room temperature over 1.5 hr. The supernatant Grignard solution was then transferred to a clean, dry flask by filtration through a glass wool plug, under a slight pressure of argon.

This Grignard solution was cooled to $-15°$ and 0.72 g of powdered cuprous chloride was added. A solution of 4.73 g of (+)-1β-tertiarybutoxy-3aα,6,7,7a-tetrahydro-7aβ-methyl-4-methylene-indan-5(4H)-one in 100 ml of dry tetrahydrofuran was then added with stirring, at $-15°$ to $-10°$, over a 20 min. period. When the addition was complete, the resulting mixture was immediately poured into 250 ml of vigorously stirred saturated $NH_4Cl$ solution. The organic layer was separated and the aqueous layer was extracted with ether. The organic phases were combined, dried ($Na_2SO_4$), filtered and concentrated at aspirator pressure. The residual oil was dissolved in benzene, washed with water and brine, dried again over anhydrous $MgSO_4$, filtered and concentrated in vacuo giving 15.18 g of a mobile, pungent-smelling oil. This material was heated on a steam bath at 0.01 mm for 30 min. to afford 9.47 g of a viscous oil.

This material was chromatographed on 50 parts of silica gel. Elution with 49:1 benzene:ethyl acetate gave 1.94g (32.1%) of oil product $[\alpha]_D^{25} + 25.85°(CHCL_3. c$ 1.18).

An analytical sample was obtained by preparative thin layer chromatography followed by evaporative distillation giving a pale yellow oil, b.p. 190°–200° (bath)/0.01 mm:$[\alpha]_D^{25} + 27.46°$ (c 1.038, $CHCl_3$).

Anal. Calcd for $C_{23}H_{34}O_3$: C, 77.05; H, 9.56. Found: C, 76.73; H, 9.73.

EXAMPLE 2 (+)-17β-tert.

Butoxy-3-methoxyestra-1,3,5(10),9(11)-tetraene

A solution of 1.56g (0.0435 mole) 83 of product prepared as in Example 1 in 150 ml of methanol was stirred rapidly, under nitrogen, while 30 ml of aqueous 10 N HCl was added in a period of 3 min. After stirring at room temperature for 3 hrs. and then with ice bath cooling for 30 min., the resulting slurry was filtered. The solid was washed three times with 15 ml portions of water and dried under vacuum giving 0.95g (64.3%) of solid product m.p. 128°–129°; $[\alpha]_D^{25} + 90.99°(c$ 1.065, $CHCl_3$); uv max ($CH_3OH$) 261 mμ (ε 16700).

Recrystallization of a sample from methanol gave colorless needles, m.p. 133°–134°: $[\alpha]_D^{25} + 101.27°(c$ 1.0526, $CHCl_3$); uv max (95% EtOH) 264 nm (ε 19700), inf. 290–300 (ε 3550). A portion of this material was sublimed prior to combustion analysis at 115°–120°/0.02 mm giving colorless solid, m.p. 132°–133°.

Anal. Calcd for $C_{23}H_{32}O_2$: C, 81.13; H, 9.47. Found: C, 81.01; H, 9.38.

EXAMPLE 3 (+)-Estrone Methyl Ether

A 0.679g (2 mmoles) sample of estratetraene prepared as in Example 2 was hydrogenated over 0.2g of pre-equilibrated 5% palladium on carbon in 25 ml of ethyl acetate at approximately 1 atmosphere. After stirring for 1.5 hr., 50 ml of hydrogen had been absorbed. The catalyst was filtered with suction and washed with ethyl acetate. Concentration of the combined filtrate and washes at aspirator pressure gave 0.741g of pale yellow oil, 17β-tert.butoxy-3-methoxyestra-1,3,5(10)-triene.

This material was dissolved in 10 ml of ice-cold trifluoroacetic acid. The resulting yellow solution was kept at 0°, under nitrogen for 20 hr. then concentrated at aspirator pressure (30°). The residue was made alkaline with aqueous 0.5 N $KHCO_3$ solution (135 ml) and stirred at room temperature for 3 hr. after the addition of 20 ml of tetrahydrofuran. Extraction with methylene chloride gave 0.77g of 3-methoxy-17β-trifluoroacetoxy-estra-1,3,5(10)-triene, which crystallized on standing. ir: (neat) 1780 (ester) $cm^{-1}$.

This product was dissolved in a mixture of 20 ml of methanol and 5 ml of 10% aqueous NaOH. The resulting solution was stirred at room temperature for 1 hr. whereupon an additional 5 ml of 10% NaOH and 10 ml of methanol were added and stirring was continued for 1.75 hr. The mixture was then treated with brine and extracted with three portions of methylene chloride. The combined methylene chloride extracts were washed with brine, dried ($MgSO_4$), filtered and concentrated giving 0.567g of estradiol 3-methylether as a pale yellow foam. ir: (neat) 3400 $cm^{-1}$ (OH).

Without purification, this compound was dissolved in 20 ml of acetone and the solution was stirred with ice bath cooling while 0.65 ml of standard Jones reagent was added over 3 min. After stirring for 5 min. with ice bath cooling, the excess oxidant was decomposed by the addition of 2 ml of 2-propanol followed by 40 ml of ice-water. The acetone was removed at aspirator pressure and the residue was extracted three times with methylene chloride. The organic extracts were combined, washed with $NaHCO_3$ solution and brine then dried ($MgSO_4$), filtered and concentrated at reduced pressure giving 0.537g of crude estrone methyl ether, as a yellow solid. Chromatography on 50g of silica gel gave 0.35 (61.7%) of essentially pure estrone methyl ether (off-white solid; eluted with 4:1 and 2:1 hexane:ether). Recrystallization from acetonitrile gave colorless solid, m.p. 164°–167°; $[\alpha]_D^{25} + 153.98°$ (c 1.00 dioxane); m.m.p. with authentic (+)-estrone methyl ether ($[\alpha]_D^{25} + 159.16°(c$ 1.00 dioxane)) 164°–167.5°.

EXAMPLE 4

(+)-Equilenin Methyl Ether

A 0.34 g (1.0 mmole) sample of pure estratetraene prepared as in Example 2 was added to 5 ml of stirred, ice-cold trifluoroacetic acid in an argon atmosphere. Argon was bubbled through the resulting yellow-green solution for 10 min. then the flask was stoppered and the reaction mixture was kept at 0° for 22 hr.

The trifluoroacetic acid was evaporated at 23°(reduced pressure) giving an orange oil that was immediately dissolved in 25 ml of tetrahydrofuran and treated with 25 ml of O.5 N aqueous $KHCO_3$ (pH 9). The resulting mixture was stirred at room temperature for 1.5 hr. Evaporation of the tetrahydrofuran at reduced pressure was followed by extraction with three portions of chloroform. The organic extracts were combined, dried ($MgSO_4$), filtered and concentrated at aspirator pressure giving 0.285 g of (+)-3-methoxy-17$\beta$-hydroxy-estra-1,3,5(10),6,8-pentaene: uv max ($CH_3OH$) 225 nm ($\epsilon$ 28400), 268 (3340), 277 (3970), 287 (3230), 309 (1460), 322 (1500), 337 (1400).

This crude alcohol was dissolved in 10 ml of acetone and the resulting solution was stirred and cooled in an ice bath while 0.5 ml of Jones reagent ($CrO_3$-$H_2SO_4$) was added dropwise. After stirring for 5 min. the excess oxidant was decomposed with 1 ml of 2-propanol. The resulting mixture was treated with ice water and most of the acetone was evaporated at reduced pressure. Extraction of the residual suspension with three portions of chloroform followed by washing the extracts with saturated $NaHCO_3$ solution then drying ($MgSO_4$), filtration and concentration at aspirator pressure gave 0.262g of partially crystalline, crude equilenin methyl ether. A combination of preparative thin layer chromatography (silica gel; benzene:ethyl acetate, 95:5) and recrystallization from methanol gave 0.0775g (27.6%) of colorless needles, m.p. 192°–194° which was essentially pure equilenin methyl ether. Another recrystallization from methanol gave colorless solid, m.p. 195°–196°, $[\alpha]_D^{25}$ + 88.72°(c 0.86, dioxane).

EXAMPLE 5

(+)-17$\beta$-Hydroxy-3-methoxyestra-1,3,5, (10),6,8-pentaene

A 1.037 g (3.05 mmoles) sample of estratetraene prepared as in Example 2 was dissolved in 15 ml of ice cold trifluoroacetic acid and the resulting brown solution was kept at 0°, under nitrogen, for 20 hr. then evaporated at aspirator pressure. The residue was dissolved in 50 ml of methanol and stirred with ice bath cooling while 25 ml of aqueous 10% NaOH solution was added followed by an additional 30 ml of methanol. After stirring at room temperature for 4 hr., the solution was poured into brine. The mixture was then extracted three times with methylene chloride. The organic extracts were combined, washed with brine, dried ($MgSO_4$), filtered and concentrated at reduced pressure giving 0.853g of a brown foam.

This crude product was chromatographed on 100g of silica gel. Elution with 9:1 benzene:ether afforder 0.255g of a gummy solid which was recrystallized from methanol giving 0.08g of pure product as colorless solid, m.p. 148°-146°. $[\alpha]_D^{25}$ + 40.16°(c 1.00, dioxane).

EXAMPLE 6

A solution of 19.5 g (0.125 mole) of m-methoxybenzylchloride dissolved in 118 ml of anhydrous tetrahydrofuran was added dropwise over a period of 45 min. to a stirred suspension of 6.25 g (0.25 mole) of magnesium turnings in 25 ml of anhydrous tetrahydrofuran at reflux temperature and under an argon atmosphere. The mixture was then stirred for 30 min. at reflux temperature. After cooling at room temperature, 250 ml anhydrous tetrahydrofuran and 11.9 g (0.062 mole) cuprous iodide were added and the mixture stirred for 5 min. The mixture was then cooled to −20°C and allowed to react under stirring at −20°C over a 5-hour period. A solution of 4.5 g (0.019 mole) of (+)-1$\beta$-tert.-butoxy-7a$\beta$-methyl-4-methylene-3a $\alpha$,6,7-,7a-tetrahydroindan-5(4H)-one in 50 ml of anhydrous tetrahydrofuran was then added with stirring at −15°C over a 30 min. period. When the addition was complete, the resulting suspension was poured into a stirred mixture of 150 ml of saturated $NH_4Cl$ solution and 100 g of ice. After stirring for 20 min., the mixture was filtered on Speedex and the residue was washed three times with 100 ml portions of ethyl ether by suction. The organic layer was separated and the aqueous layer was extracted two times with 500 ml portions of ethyl ether. The organic phases were combined, dried over sodium sulphate, filtered and concentrated ona Rotovap at 50°C bath temperature under water pump vacuum. The residual viscous oil, 19.97 g, was chromatographed on 200 parts of silica gel. Elution with 50:1 benzene:ethylacetate afforded 6.025 g of (+)-1$\beta$-tert.-butoxy-4[2-(3-methoxyphenyl)ethyl]-7a$\beta$-methyl-3a$\alpha$,4,7,7a-tetrahydroindan-5(6H)-one as a viscous oil.

EXAMPLE 7

A solution of 5.8 g (0.025 mole) of m-benzyloxybenzyl chloride dissolved in 25 ml of anhydrous tetrahydrofuran was added dropwise over a period of 30 min. to stirred suspension of 1.25 g (0.05 mole) of magnesium turnings in 5 ml of anhydrous tetrahydrofuran at reflux temperature and under an argon atmosphere. The mixture was then stirred for 30 min. at reflux temperature. After cooling at room temperature, 100 ml of anhydrous tetrahydrofuran and 0.96 g (0.005 mole) of cuprous iodide were added and the mixture was stirred for 2 hours at −20°C. A solution of 1.113 g (0.0047 mole) of (+)-1$\beta$-tert.-butoxy-7a$\beta$-methyl-4-methylene-3a$\alpha$,6,7,7a-tetrahydroindan-5(4H)-one in 10 ml of anhydrous tetrahydrofuran was then added with stirring at −20°C over a 10 min. period. When the addition was complete, the resulting suspension was poured into a stirred mixture of 50 ml 1 N sulfuric acid and 50 g of ice. After stirring for 5. min., the mixture was extracted three times with 100 ml of ethyl acetate. The organic phases were combined, washed with saturated sodium chloride solution, dried over anhydrous sodium sulphate, filtered and concentrated on the Rotovap at 50°C bath temperature under water pump vacuum. The residual oil containing (+)-1$\beta$-tert.butoxy-3a$\alpha$,4,7,7a-tetrahydro-4-[2-(3-benzyloxyphenyl)-ethyl]-7a$\beta$-methyl-5(6H)-indanone (5.7 g) was dissolved in 250 ml of methanol, 50 ml of 1N hydrochloric acid and 100 ml of dichloromethane and stirred over a 12-hour period at room temperature. The resulting mixture was poured into 500 ml of water and extracted three times with 200 ml of dichloromethane. The organic extracts were combined, dried over anhydrous sodium sulphate, filtered and concentrated at 40°C under water pump vacuum. The residual oil (5.356 g) was chromatographed on 120 parts of silica gel suspended in n-hexane. Elution with a 1:1 mixture (v/v) of n-hexane and dichloromethane gave 0.995 g of (+)-3-benzyloxy-17β-tert.-butoxy-estra-1,3,5(10),9(11)-tetraene, which after crystallization from methanol melts at 84°–85°C; $[\alpha]_D^{25}$ + 62°(c 0.1, dioxane).

EXAMPLE 8

A solution of 78 g (0.5 mole) of m-methoxybenzyl chloride dissolved in 430 ml of anhydrous tetrahydrofuran was added dropwise over a period of 55 min. to a stirred suspension of 24.3 g (1 mole) of magnesium turnings in 100 ml of anhydrous tetrahydrofuran at reflux temperature and under an argon atmosphere. The mixture was then stirred for 30 min. at reflux temperature. After cooling at room temperature, 2000 ml of anhydrous tetrahydrofuran and 15.85 g (0.16 mole) of cuprous iodide were added and the mixture was stirred for 30 min. at room temperature. A solution of 23.6 g (0.1 mole) of (+)-1β-tert.-butoxy-7aβ-methyl-4-methylene-3aα,6,7,7a-tetrahydroindan-5(4H)-one in 200 ml of anhydrous tetrahydrofuran was then added with stirring over a 15-min. period. When the addition was complete, the resulting suspension was poured into a stirred mixture of 1000 ml of 1 N sulfuric acid and 1000 g of ice. After stirring for 5 min., the mixture was extracted three times with 1000 ml of ether. The organic phases were combined, washed three times with 500 ml of water, dried over 600 g of anhydrous sodium sulphate (1 hour), filtered and concentrated at 40°–45°C bath temperature under water pump vacuum. The residual oil, 80 g, was dried at this temperature for 15 min. under a vacuum of 11 Torr and then dissolved in 3000 ml of ethanol. Within 15 min., 600 ml of 10 N hydrochloric acid were added with cooling, the temperature not exceeding 20°C. The faintly turbid solution was stirred at 20°C for 4 hrs and then allowed to stand at a temperature of 0°C for 12 hrs. The suspension was filtered by suction, the residue being washed five times with 1000 ml of water and dried at 80°C/15 Torr for 4 hrs. The crude crystals were dissolved in 200 ml of ether, the solution was diluted with 300 ml of ethanol, then 200 ml of the solvent was distilled off. The residual solution was left at 20°C for 2 hrs during which period crystallization occurred. The crystals were filtered off with suction, washed with a total of 100 ml of ice-cold methanol and dried at 25°C (3 hrs. at 11 Torr and 9 hrs. at 0.01 Torr). 24.15 g of (+)-17β-tert.-butoxy-3-methoxyestra-1,3,5(10),9(11)-tetraene were obtained, melting point 131°–132° C.

EXAMPLE 9

(+)-1β-tert.Butoxy-7aβ-ethyl-3aα,4α,7,7,a-tetrahydro-4β-[2-(3-methoxyphenyl)ethyl]-5(6H)-indanone and (+)-1β-tert.

Butoxy-7aβ-ethyl-3aα, 4β,7,7a-tetrahydro-4α-[2-(3-methoxyphenyl)ethyl]-5(6H)-indanone A 4.96 g (0.2 mole) sample of magnesium turnings was heated at 120° for 0.5 hr then cooled to room temperature whereupon 20 ml of dry THF was added. The resulting slurry was stirred and heated at reflux while a solution of 15.6 g (0.1 mole) of m-methoxybenzyl chloride in 85 ml of dry THF was added dropwise over a 2 hr period. After stirring at reflux for 0.5 hr, the dark mixture was cooled to 25°(ice bath) and 400 ml of dry THF was added followed by 3.17 g (0.032 mole) of cuprous chloride powder. A 6° exotherm was noted upon addition of the cuprous chloride. The resulting mixture was stirred at room temperature for 0.75 hr then a solution of 5.01 g (0.02 mole) of crude (+)-1β-tert. butoxy-7aβ-ethyl-3aα,6,7,7a-tetrahydro-4-methylene-indan-5(4H)-one in 40 ml of dry THF was added over a 15 min period. After stirring at room temperature for 5 min. the resulting solution was decanted from the residual metal into a stirred mixture of 200 ml of 1 N aqueous $H_2SO_4$ and 200 g of ice. Stirring was continued for 5 min then ether was added and the organic layer was separated. The aqueous layer was extracted four times with ether then the organic solutions were combined, washed with water and brine and dried. Concentration in vacuo afforded 17.2 g of residue.

This material was chromatographed on 400 g of silica gel. The early fractions eluted with 9:1 hexane: ether afforded 3.16 g of the 4β-H epimer in essentially pure form as a viscous oil. A sample of this material was rechromatographed on silica gel and evaporatively distilled giving the analytical specimen as a viscous, pale-yellow oil, bp 160°–180°(bath temperature) 0.2 mm. $[\alpha]_D^{25}$ + 11.93°(c. 1.2488, $CHCl_3$); ir ($CHCl_3$) 1705, 1600, 1585 $cm^{-1}$; uv max (95% EtOH) 217 nm (ε 7946), 272 (1980), 278 (1860); nmr ($CDCl_3$) δ 7.15 (m, 1), 6.72 (m, 3), 3.75 (s, 3), 3.48 (t, 1, J = 8 Hz), 1.12 ppm (s); ms m/e 372 ($M^+$).

Anal. Calcd for $C_{24}H_{36}O_3$: C, 77.38; H, 9.74. Found: C, 77.25; H, 9.85.

The later fractions eluted with 9:1 hexane:ether yielded 1.4 g of a mixture of the 4β-H epimer (minor; less polar on tlc) and the 4α-H epimer (major; more polar on tlc). This material was rechromatographed on silica gel. Later fractions eluted with 9:1 hexane:ether furnished 0.51 g of essentially pure (tic) 4α-H epimer as a viscous, colorless oil. $[\alpha]_D^{25}$ + 17.96°(c 1.0468, $CHCl_3$); uv max (95% EtOH) 215 nm (ε 7970), 273 (1990), 279 (1870); ir ($CHCl_3$) 1700, 1600, 1585 $cm^{-1}$; nmr ($CDCl_3$) δ 7.15 (m, 1), 6.70 (m, 3), 3.75 (s, 3), 3.43 (m, 1), 1.10 ppm (s); ms m/e 372 ($M^+$).

Anal. Calcd for $C_{24}H_{36}O_3$: C, 77.38; H, 9.74. Found: C, 77.53; H, 9.84.

EXAMPLE 10

Epimerization of 4α-H epimer

A 54 mg sample of 4α-H epimer from Example 9 was treated with 5 ml of a solution prepared by diluting 5 ml of 1 N aqueous NaOH to 50 ml with methanol. The mixture was heated for 5 min. on a steam bath in order to effect solution. After cooling to room temperature, tlc analysis indicated that epimerization was complete as evidenced by the essential absence of the spot due to the more polar, 4α-H epimer. After standing at room temperature for 1.25 hr, the solution was diluted with methylene chloride and toluene then dried, filtered and concentrated in vacuo. There was obtained 54 mg of colorless oil, the tlc mobility which was identical to that of the 4β-H epimer. The latter substance was unchanged by alkali treatment.

EXAMPLE 11

(+)-17β -tert.Butoxy-13β -ethyl-3-methoxygona-1,3,5(10),9(11)-tetraene

A solution of 7.28 g (19.6 mmole) of (+) -1β-tert.butoxy-7aβ-ethyl-3aα,4β,7,7a-tetrahydro-4α-[2-(3- methoxyphenyl)ethyl]-5-(6H)-indanone in 675 ml of methanol was stirred at room temperature while 135 ml of 10 N aqueous HCl was added dropwise over a 0.5 hr period. The temperature rose to 34° during the addition. The resulting cloudy mixture was seeded with an authentic crystal of product and stirred at room temperature for 4 hr during which time a solid precipitated. After cooling to 5°(ice bath) and stirring for an additional 15 min the slurry was filtered with suction and the solid was washed with water. The solid was then dried under high vacuum at 40°–50° overnight giving 5.86 g of colorless solid, m.p. 116°–119°, $[\alpha]_D^{25}$ +92.10°(c 1.0239, CHCl₃); uv max (95% EtOH) 263 nm (ε 20000), sh 297 (3600), infl 310 (2100). A 1g sample of this material was recrystallized from ethanol giving 0.91 g of colorless needles, m.p. 120°–121°. $[\alpha]_D^{25}$ + 97.13° (c, 1.0285, CHCl₃); uv max (95% EtOH); 263 nm (ε 19780), 298 (3150), infl 310 (2120); ir (CHCl₃) 1640, 1615, 1580, 1505, 1375, 1245 cm⁻¹; nmr (CDCl₃)δ 7.45 (d, 1), 6.63 (m, 2), 6.06 (m, 1), 3.73 (s, 3), 3.58 (m, 1), 1.14 ppm (s); ms m/e 354 (M⁺).

Anal. Calcd for $C_{24}H_{34}O_2$: C, 81.31; H, 9.67. Found: C, 81.37; H, 9.66.

EXAMPLE 12

(+)-17β-tert.Butoxy-13β-ethyl-3-methoxygona-1,3,5(10)-triene

A mixture of 1g (2.82 mmoles) of (+)-17β-tert.butoxy-13β-ethyl-3-methoxygona-1,3,5(10),9(11)-tetraene, 0.25 g of 5% palladium on carbon and 25 ml of ethyl acetate was stirred in an atmosphere of hydrogen for 1 hr during which time a total of 74 ml of hydrogen was absorbed (70.5 ml theory). The catalyst was filtered with suction on Celite and the filter cake was washed well with ethyl acetate. Concentration of the combined filtrate and washes in vacuo gave 1.23 g of colorless solid. This material was chromatographed on 50 g of silica gel. Elution with 19:1 hexane:ether gave 0.925 g of colorless solid which recrystallized ethanol. This afforded 0.67 g of colorless plates, m.p. 121°-123°. $[\alpha]_D^{25}$ + 44.69°(c 1.016, CHCl₃); uv max (95% EtOH) 278 nm (ε 2020), 287 (1860); ir (CHCl₃) 1610, 1580, 1500, 1360 cm⁻¹; nmr (CDCl₃)δ 7.18 (m, 1), 6.68 (m, 2), 3.74 (s, 3), 3.51 (t, 1, J = Hz), 1.15 ppm (s); ms m/e 356 (M⁺).

Anal Calcd for $C_{24}H_{36}O_2$: C, 80.85; H, 10.18. Found: C, 80.71; H, 10.17.

EXAMPLE 13

(+)-13β-Ethyl-3-methoxygona-1,3,5(10)-trien-17-one

A solution of 0.4 g (1.12 mmoles) of (+)-17β-tert.butoxy-13β-ethyl-3-methoxygona-1,3,5(10)-triene and 0.1 g of p-toluenesulfonic acid monohydrate in 10 ml of toluene was stirred and heated at reflux for 1 hr. The resulting solution was cooled and treated with saturated aqueous sodium bicarbonate solution then extracted twice with ether. The combined organic extracts were dried, filtered and concentrated in vacuo giving 0.348 g of (+)-17β-hydroxy-13β-ethyl-3-methoxygona-1,3,5(10)-triene as a colorless solid.

This material was dissolved in 10 ml of acetone and the resulting solution was stirred with ice bath cooling while 0.4 ml of Jones reagent was added dropwise from a syringe over a 5-min. period. After stirring at 0°–5° for 2 min., the red mixture was decomposed by the addition of 10% aqueous sodium bisulfite solution. The resulting green mixture was diluted with water and extracted three times with ether. The ether extracts were combined, washed once with brine then dried, filtered and concentrated in vacuo giving 0.334 g of crude product as a tan solid. This material was chromatographed on 20 g of silica gel. Fractions eluted with 4:1 hexane:ether afforded 0.274 g of colorless solid. Recrystallization from 1:1 cyclohexane:ethyl acetate furnished 0.207 g of colorless plates, m.p. 148.5°–150°. $[\alpha]_D^{25}$ + 102.37° (c 1.0257, CHCl₃); + 102.82°(c 1.0329, 1:1 CHCl₃:CH₃OH).

EXAMPLE 14

(+)-17β-tert.Butoxy-3-methoxyestra-1,3,5(10)-triene

A mixture of 0.8 g (2.35 mmoles) of (+)-17β-tert.butoxy-3-methoxyestra-1,3,5(10),9(11)-tetraene, 0.25 g of 5% palladium on carbon and 30 ml of ethyl acetate was stirred in an atmosphere of hydrogen for 1.33 hr. At the end of this time, 61 ml of hydrogen had been absorbed (59 ml theory). The catalyst was filtered with suction on Celite and the filter cake was washed with ethyl acetate. The filtrate and washes were combined and concentrated in vacuo giving 0.831 g of colorless oil which crystallized on standing at 0°. Recrystallization from ethanol yielded 0.433 g of product as colorless crystals, m.p. 91°–92.5°; ir (CHCl₃) 1610, 1580, 1500, 1360 cm⁻¹; uv max (95% EtOH) 277 (ε 2030), 285 (1900); nmr (CDCl₃) δ 7.20 (m, 1), 6.63 (m, 2), 3.73 (s, 3), 3.43 (t, 1, J = 8 Hz), 1.15 (s), 0.75 ppm (s, 3); ms m/e 342 (M⁺). A sample of this material was sublimed (110°–120°/0.15 mm) prior to combustion analysis giving colorless solid m.p. 90°–92°. $[\alpha]_D^{25}$ +62.20° (c 1.0176, CHCl₃).

Anal. Calcd for $C_{23}H_{34}O_2$: C, 80.65; H, 10.00. Found: C, 80.88; H, 9.91.

I claim:

1. A process for the preparation of a compound of the formula

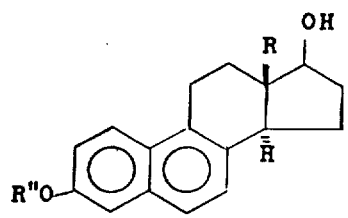

wherein R is lower alkyl and R'' is lower alkyl, tertiary lower alkyl, benzyl, diphenylmethyl, or trityl, which comprises contacting a compound of the formula

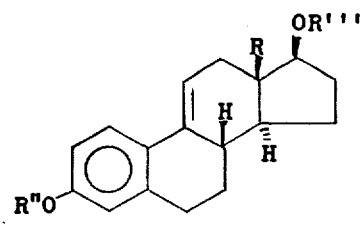

wherein R and R'' are as above and R''' is tertiary lower alkyl,
with a strong acid selected from the group consisting of mineral acids, organic sulfonic acids and trifluoroacetic acid and, where trifluoroacetic acid is employed, hydrolyzing the 17-trifluoroacetate of reaction product with aqueous base.

2. The process of claim 1 wherein R is methyl or ethyl, R'' is methyl and R''' is tertiary butyl.

3. The process of claim 1 wherein trifluoroacetic acid is employed and where the basic hydrolysis is effected by means of aqueous alkali metal bicarbonate, carbonate or hydroxide.

4. The process of claim 3 wherein the acid treatment step is carried out at between about −10° and +30°C.

* * * * *